United States Patent [19]

MacFarlane et al.

[11] Patent Number: 5,198,226

[45] Date of Patent: Mar. 30, 1993

[54] LONG ACTING NICARDIPINE HYDROCHLORIDE FORMULATION

[75] Inventors: Calum B. MacFarlane, Linlitchgow; Alastair B. Selkirk, Edinburgh; Michael J. Dey, East Calder, all of Scotland

[73] Assignee: Syntex (U.S.A.) Inc., Palo Alto, Calif.

[21] Appl. No.: 794,356

[22] Filed: Nov. 12, 1991

Related U.S. Application Data

[60] Continuation of Ser. No. 526,862, May 22, 1990, abandoned, which is a division of Ser. No. 57,469, Jul. 26, 1987, Pat. No. 4,940,556, which is a continuation-in-part of Ser. No. 940,878, Dec. 10, 1986, abandoned, which is a continuation-in-part of Ser. No. 823,896, Jan. 30, 1986, abandoned.

[51] Int. Cl.$^5$ .................... A61K 9/52; A61K 31/44
[52] U.S. Cl. .................... 424/457; 424/451; 424/501; 424/456; 514/356
[58] Field of Search ............... 424/451, 457, 458, 501; 514/356

[56] References Cited

U.S. PATENT DOCUMENTS

| | | | |
|---|---|---|---|
| Re. 27,214 | 11/1971 | Nakahara | 264/15 |
| 3,390,050 | 6/1968 | Speiser | 167/83 |
| 3,758,679 | 9/1973 | Seidler | 424/19 |
| 3,985,758 | 10/1976 | Murakami et al. | 260/295.5 |
| 4,343,789 | 8/1982 | Kawata et al. | 424/78 |
| 4,404,183 | 9/1983 | Kawata et al. | 424/19 |
| 4,412,986 | 11/1983 | Kawata et al. | 424/80 |
| 4,562,069 | 11/1985 | Hegasi et al. | 424/80 |
| 4,665,100 | 5/1987 | Ludwig | 514/778 |
| 4,765,990 | 8/1988 | Sugimoto et al. | 424/484 |

FOREIGN PATENT DOCUMENTS

| | | |
|---|---|---|
| 1180277 | 1/1985 | Canada . |
| 1184118 | 3/1985 | Canada . |
| 0022631 | 2/1980 | European Pat. Off. . |
| 0047899 | 3/1982 | European Pat. Off. . |
| 0142561 | 3/1983 | European Pat. Off. . |
| 0078430 | 5/1983 | European Pat. Off. . |
| 0204596 | 12/1986 | European Pat. Off. . |
| 0324982 | 12/1988 | European Pat. Off. . |
| 0001247 | 4/1989 | European Pat. Off. . |
| 3419128 | 11/1985 | Fed. Rep. of Germany . |
| 109411 | 6/1983 | Japan .................... 514/356 |
| 0109412 | 6/1983 | Japan . |
| 2159407 | 12/1985 | United Kingdom . |

OTHER PUBLICATIONS

Sugimoto (Kanebo, Ltd.) CA 102, 19116r (1985) PCT WO 8503440 Jul. 13, 1984 Long Acting Nifedipine Preparation.

Hasegawa et al. I CA 101, 157544g (1984) of Yakugaku Zasshi (1984) Solid Dispersion Obtained from Nifedipine and an Enteric Coating Agent I.

Hasegawa et al. II, CA 102, 190156m (1985) of Chem. Pharm. Bull. 33(1), 338–91 Bioavailability and stability of nifedipine–enteric coating agent solid dispersion.

Hasegawa et al. III, CA 103, 1190y (1985) of Chem. Pharm. Bull. 33(4), 1615–19 Application of solid dispersions of nifedipine with enteric coating agent to prepare a sustained-release dosage form.

Hasegawa et al., IV, CA 103, 128905m (1985) of Yakugaku Zasshi 1985, 105(6), 586–92; Dissolution mechanism of solid dispersions of nifedipine with enteric–coating agents.

Hasegawa et al, V, CA 103, 183487b (1985) of Chem. Pham. Bull. 1985, 33(8), 3429–35; Physical properties of solid dispersions of poorly water–soluble drugs with enteric coating agents.

Chiou et al., J. Pharm. Sci., 60(9), 1281–1302 (1971); Pharmaceutical Applications of Solid Dispersion Systems.

N. Kohri et al. J. Pharm. Sci., 75(1), 57–61 (1986), "Sustained Release of Nifedipine from Granules".

Chemical Abstract, 104(20), 391 (1986), No. 174662y.

Remington's Pharm. Sci., 15th ed. (1975) 1560–1565.

J. W. Conine et al., D&C, 34–81 (Apr. 1970), "Preparation of Small Solid Pharmaceutical Spheres".

Primary Examiner—Thurman K. Page
Assistant Examiner—Neil Levy
Attorney, Agent, or Firm—David A. Lowin; Tom M. Moran; Cathleen M. Desjardins

[57] ABSTRACT

A long acting sustained release pharmaceutical composition for dihydropyridine calcium channel blockers wherein the calcium channel blocker and a pH-dependent binder are intimately admixed in essentially spherically shaped non-rugose particles of up to 1.2 mm in diameter.

10 Claims, 5 Drawing Sheets

LONG ACTING NICARDIPINE HYDROCHLORIDE FORMULATION

This is a continuation of application Ser. No. 07/526,862, filed May 22, 1990 now abandoned which is a division of Ser. No. 07/057,469, filed Jul. 26, 1987, now U.S. Pat. No. 4,940,556; which in turn was a continuation-in-part of Ser. No. 940,878, filed Dec. 10, 1986, now abandoned; which in turn was a continuation-in-part of Ser. No. 823,896, filed Jan. 30, 1986, now abandoned, all incorporated herein by reference.

BACKGROUND OF THE INVENTION

This invention concerns long acting sustained release pharmaceutical compositions and dosage forms for dihydropyridine calcium channel blockers.

Calcium channel blockers are a relatively recently discovered class of compounds which possess a wide spectrum of properties useful in the treatment of cardiovascular and cerebrovascular disorders. Among the clinical applications for which this class of compounds has shown some useful therapeutic properties are the treatment of classic exertional angina, vasospastic angina, angina pectoris, acute myocardial infarction, cardiac arrhythmias, systemic arterial hypertension, pulmonary arterial hypertension, and cardiomyopathies.

Several structural classes of compounds are known which exhibit calcium channel blocking utility. Compounds representative of some of these classes include nicardipine, verapamil, diltiazam, perhexiline and lidoflazine.

The structural class of calcium channel blockers of interest in this invention, of which nicardipine is a member, are 1,4-dihydropyridine-3,5-dicarboxylic acid derivatives of the general formula A:

(A)

in which AR is a simple or fused aryl or heteroaryl ring moiety; X is hydrogen or one or more substituents on the AR moiety; $R_7$ and $R_8$ are independently hydrogen or ester forming moieties; $R_9$ and $R_{10}$ are independently methyl or various other 2 and 6 position substituents on the dihydropyridine ring, and R is hydrogen or an alkyl or simple aryl group. Examples of AR groups include, but are not limited to phenyl, pyridinyl, benzofurazanyl, benzoxadiazolyl and the like. Examples of X groups include, but are not limited to alkyl, halo, haloalkyl, alkoxy, haloalkoxy, alkoxycarbonyl, alkenyl, methylenedioxy, ethylenedioxy, nitro, cyano and the like. Examples of $R_7$ and $R_8$ ester forming moieties include, but are not limited to alkyl, alkoxy, haloalkyl, nitro, hydroxyalkyl, alkylenyloxyalkyl, phenylaminoalkyl, alkylaminoalkyl or alkoxyaminoalkyl, amino(carbonyl)oxyalkyl, or an optionally substituted simple or fused aryl, aralkyl or arylsulfonyl group such as, but not limited to, phenyl, phenylalkyl, phenylsulfonyl, phenalkenyl, naphthyl, naphthylalkyl, dioxaphosphorinanyl, piperidinyl, pyrrolidinyl, furyl, pyrrolyl, pyridyl, imidazolyl, thienyl, morpholinyl, [(tetrahydropyran-2-yloxy)-alkyl]phenoxyalkyl or [(tetrahydropyran-2-yloxy)- alkyl]phenylthioalkyl. Examples of $R_9$ and $R_{10}$ substituents include, but are not limited to alkyl such as methyl, a substituted alkyl group such as hydroxyalkyl or aminoalkoxyalkyl, cyano, or optionally substituted phenylcarbonylalkyl; Examples of R groups other than hydrogen include, but are not limited to alkyl, benzyl, morpholinyl and morpholinylalkyl.

Many compounds within the general class represented by formula A are known and have been shown to have calcium channel blocking activity. It is known, for example, that 4-(2'-nitrophenyl)-2,6-dimethyl-1,4-dihydropyridine-3,5-dicarboxylic acid dimethyl ester shows calcium channel blocking activity (U.S. Pat. No. 3,644,627). Other compounds within this structural and pharmacologic class include those disclosed in U.S. Pat. No. 3,511,837 (4-pyrimidyl-1,4-dihydropyridine derivatives), U.S. Pat. No. 3,691,177 (cyanophenyl-1,4-dihydropyridine derivatives), German Offlegungsschrift No. 1,813,436 (N-alkyl-1,4-dihydropyridine derivatives), No. 1,963,185 (4-nitro and other group substituted phenyl-1,4-dihydropyridine derivatives), No. 1,963,186 (sulfur containing 4-aryl-1,4-dihydropyridine derivatives), No. 2,005,116 (1,4-dihydropyridine-3,5-dicarboxylic acid unsaturated alkyl esters), No. 2,3,146 (3-alkanoyl-1,4-dihydropyridine-5-carboxylic acid esters, U.S. Pat. No. 3,511,837 (1,4-dihydro-2,6-dimethyl-4-(2'-trifluoromethylphenyl)-3,5-pyridine dicarboxylic acid diethyl ester) and in BE 862-107, U.S. Pat. No. 4,017,629, DE 2,616,995, and German Offenlegungsschrift 3,501,695 (various 3-arylsulfonyl 1,4-dihydropyridine derivatives). Other 1,4-dihydropyridine compounds with cardiovascular activity are disclosed in U.S. Pat. Nos. 3,644,627 and 3,485,847, in German Offenlegungsschrift 1,670,827 and in Bundesrepublik Deutschland Auslegeschrift 17,92,764.

Specific compounds of formula A which can be incorporated in the long acting sustained release composition of this invention include 2,6-dimethyl-3-carbomethoxy-4-(3-nitrophenyl)--5-[3-(4-[2-(tetrahydropyran-2-yloxy)ethyl]phenoxy)-propoxy carbonyl]-1,4-dihydropyridine disclosed in U.S. application Ser. No. 874,264 filed Jun. 13, 1986, now U.S. Pat. No. 4,761,420, which is incorporated by reference herein; 3,5-pyridinedicarboxylic acid, 2-[(2-aminoethoxy)methyl]-4-(2-chlorophnyl)-1,4-dihydro-6-methyl, 3-ethyl 5-methyl ester, (±)-, (Z)-2-butenedioate, generic name: amlodipine; 3,5-pyridinedicarboxylic acid 4-(4-benzofurazanyl)-1,4-dihydro-2,6-dimethyl-, diethyl ester, generic name: darodipine; 3,5-pyridinedicarboxylic acid, 1,4-dihydro-2,6-dimethyl-1-[2-(4-morpholinyl)ethyl]-4-[2-(trifluoromethyl)phenyl]-, diethyl ester, generic name: flordipine; 1,4-dihydro-2,6-dimethyl-4-(2-trifluoromethylphenyl)-3,5-pyrinedicarboxylic acid 2-([1-(4-hydroxyphenyl)-3-oxo-propyl]amino)ethyl ester), generic name: iodipine; isopropyl methyl 4-(4-benzofurazanyl)-1,4-dihydro-2,6-dimethyl-3,5-pyridine dicarboxylate, generic name: isrodipine; diethyl 1',4'-dihydro-2',6'-dimethyl-2-(methylthio)[3,4'bipyridine]-3'5'-dicarboxylate, generic name: mesudipine, 3,5-pyridinedicarboxylc acid, 2-cyano-1,4-dihydro-6-methyl-4-(3-nitrophenyl)-, 3-methyl 5-(1-methylethyl)ester, generic name: nilvadipine; ethyl methyl 1,4-dihydro-2,6-dimethyl-4-[2,3-(methylenedioxy)phenyl-3,5-pyridinedicarboxylate, generic name: oxodipine; dimethyl 4-[0-(di-fluoromethyl)phenyl]-1,4-dihydro-6-dimethyl-3,5-pyridine dicarboxylate, generic name: riodipine; methyl 2,6-dimethyl-4-(2-nitrophenyl)-

5-(2-oxo-1,3,2-dioxaphosphorinan-2-yl)-1,4-dihydropyridine 3-carboxylate; 1,4-dihydro-2-hydromethyl-4-(m-nitrophenyl)-6-methyl-3,5-pyridine dicarboxylc acid diethyl ester; methyl (E)-3-phenyl-2-propeny-1-yl-1,4-dihydro-2,6-dimethyl-4-(3-nitrophenyl)pyridine-3,5-dicarboxylate; (E)-4-(2-(3-(1,1-dimethylethoxy)-3-oxo-1-propenyl)phenyl-1,4-dihydro-2,6-dimethyl-3,5-pyridinedicarboxylic acid, diethyl ester; 1,4-dihydro-2,6-dimethyl-4-(3-nitrophenyl)-3,5-pyridinedicarboxylic acid methyl 1-(phenylmethyl)-3-piperidinyl ester monohydrochloride; 3-(2-furoyl)-5-methoxycarbonyl-2,6-dimethyl-4-(2-nitrophenyl)-1,4-dihydropyridine; 3,5-pyridinedicarboxylic acid 2-(((aminocarbonyl)oxy)methyl)-4-(2,3-dichlorophenyl)-1,4-dihydro-6-methyl-5-methyl 3-(1-methylethyl)ester; 1-benzyl-3-pyrrolidinyl methyl 2,6-dimethyl-4-(m-nitrophenyl)-1,4-dihydropyridine-3,5-dicarboxylate; and isopropyl 4-(2,1,3-benzoxadiazol-4-yl)-1,4-dihydro-2,6-dimethyl-5-nitro-3-pyridinecarboxylate.

Calcium channel blockers of particular interest in this invention are compounds selected from the group represented by the formula:

(1)

where;
R$_1$ is —NO$_2$, —CF$_3$, or halo;
R$_2$ is alkyl or —CH$_2$CH$_2$OCH$_3$; and
R$_6$ is hydrogen or alkyl; and
R$_3$ is alkyl, alkylenyloxyalkyl, haloalkyl, optionally substituted phenyl alkyl, optionally substituted napthyl alkyl, or in which:
A is alkylene;
R$_4$ is alkyl, alkoxy, or optionally substituted phenyl or phenyl alkyl; and
R$_5$ is hydrogen or alkyl;
and the pharmaceutically acceptable salts thereof.

Several compounds within this group are known to possess a high degree of calcium channel blocking activity. These include, for example, 4-(2'-nitrophenyl)-2,6-dimethyl-1,4-dihydropyridine-3,5-dicarboxylic acid dimethyl ester, generic name: nifedipine (U.S. Pat. No. 3,644,627); 4-(3'-nitrophenyl)-2,6-dimethyl-1,4-dihydropyridine-3,5-dicarboxylic acid di-n-propyloxyethyl ester, generic name: niludipine; 4-(3'-nitrophenyl)-2,6-dimethyl-1,4-dihydropyridine-3,5-dicarboxylic acid 3-ethyl ester 5-methyl ester, generic name: nitrendipine; 4-(3'-nitrophenyl)-2,6-dimethyl-1,4-dihydropyridine-3,5-dicarboxylic acid 3-methyl ester 5-(2-methoxyethyl)ester, generic name: nimodipine; 4-(2'-nitrophenyl)-2,6-dimethyl-1,4-dihydropyridine-3,5-dicarboxylic acid 3-methyl ester 5-isobutyl ester, generic name: nisoldipine; 4-(2',3'-dichloro)-2,6-dimethyl-1,4-dihydropyridine-3,5-dicarboxylic acid 3-ethyl ester 5-methyl ester, generic name: felodipine; 4-(3'-nitrophenyl)-2,6-dimethyl-1,4-dihydropyridine-3,5-dicarboxylic acid 3-methyl ester 5-β-(N-benzyl-N-methylamino)-ethyl ester, generic name: nicardipine; isopropyl methyl 1,4-dihydro-2,6-dimethyl 4-(3-nitrophenyl)-3,5-pyridine dicarboxylate; and 2,6-dimethyl-3,5-diethoxycarbonyl-4-(o-difluoromethylphenyl)-1,4-dichydropyridine.

Other compounds of Formula I which can be practically administered from the long acting sustained release compositions of this invention include 2,6-dimethyl-3,5-bis(methoxycarbonyl)-4-phenyl-1,4-dihydropyridine, 2,6-dimethyl-3,5-bis(methoxycarbonyl)-4-(3-methylphenyl)-1,4-dihydropyridine, 2,6-dimethyl-3,5-bis(methoxycarbonyl)-4-(3-cyanophenyl)-1,4-dihydropyridine, 2,6-dimethyl-3,5-bis(methoxycarbonyl)-4-(3-nitrophenyl)-1,4-dihydropyridine, 2,6-dimethyl-3,5-bis(methoxycarbonyl)-4-(4-nitrophenyl)-1,4-dihydropyridine, 2,6-dimethyl-3,5-bis(methoxycarbonyl)-4-(4-methylphenyl)-1,4-dihydropyridine, 2,6-dimethyl-3,5-bis(methoxycarbonyl)-4-[4-(dimethylamino)phenyl]-1,4-dihydropyridine, 2,6-dimethyl-4-phenyl-1,4-dihydropyridine 3,5-dicarboxylacid diethyl ester, 2,6-dimethyl-3,5-bis(methoxycarbonyl)-4-(2,4-dinitrophenyl)-1,4-dihydropyridine, 2,6-dimethyl-3,5-bis(methoxycarbonyl)-4-[2-(trifluoromethyl)phenyl]-1,4-dihydropyridine, and 2,6-dimethyl-3,5-bis(methoxycarbonyl)-4-(pentafluorophenyl)-1,4-dihydropyridine, all of which are disclosed in J. Med. Chem (1986) 29 (12), pp. 2504–2511.

Calcium channel blockers of the 1,4-dihydropyridine class share a number of pharmacological and pharmacokinetic properties in common which render them well suited to administration by the long acting sustained release methods of this invention. They are drugs which are extensively lipid-soluble and therefore are widely and extensively distributed within body tissues at steady state. They are also rapidly absorbed after oral administration, showing peak plasma levels within approximately about one hour (T$_{max}$). The half-life of elimination of these compounds is generally in the range of two to five hours, thus necessitating administration of standard oral dosage forms three to four times daily. Additionally, some of the compounds, in particular, nicardipine, undergo extensive first pass metabolism.

The pharmaceutical compositions and dosage forms of this invention are particularly well suited for the administration of nicardipine and its pharmaceutically acceptable salts, such as nicardipine hydrochloride. The preparation and use of nicardipine and other closely related compounds and their pharmaceutically acceptable salts are described in U.S. Pat. No. 3,985,758 which is incorporated by reference herein.

At the present time, the preferred route of administration for most therapeutic applications of the dihydropyridine calcium channel blockers is via an oral dosage form. These are typically compressed tablets, hard gelatin capsules filled with a powder mix, or soft gelatin capsule filled with a solution, and are conventionally administered three or four times daily.

However, conventional release oral dosage forms are poorly suited to dihydropyridine calcium channel blocker therapy. At the acid pH that occurs in the stomach, the solubility of the basic dihydropyridines is relatively high, resulting in rapid dissolution and absorption. As the pH increases along the gastrointestinal tract, dihydropyridine solubility, and hence the dissolution rate, decreases. As a result, conventional release oral dosage forms release calcium channel blocker more rapidly in the more acidic stomach region and less rapidly in the less acidic intestinal region. The release profiles of such dosage forms are inherently dependent upon the location of the calcium channel blocker within the gastrointestinal tract.

There is a need, therefore, for a long acting dosage form with sustained release properties capable of providing therapeutic calcium channel blocker plasma concentrations when the dosage form is administered less frequently, preferably once or twice daily. In addition to providing convenience for the patient, such a sustained release dosage form would minimize undesirable fluctuations in drug plasma concentration.

In U.S. Pat. No. 4,343,789, formulations and dosage forms for nicardipine and related compounds are described which provide some dissolution control, and hence sustained release of the drug. As described in the patent, a powder containing amorphous nicardipine, polyethylene oxide, and other excipients is formed which can then be formed into granules, tablets, pills or capsules by conventional means. The formulation requires that the nicardipine or salt thereof be in amorphous form, and be combined with polyethylene oxide in a fine particle powder or granules. The formulation may additionally contain a pH-dependent agent for dissolution control, such as a copolymer of methacrylic acid and a methacrylic acid ester. While the specific disclosure is primarily directed to tablet formulations, one capsule dosage form is disclosed which contains small coated pills, part of which are film coated, and part of which are coated with Eudragit (methacrylic acid/methyacrylic acid ester copolymer).

However, the preparation of the drug in amorphous form, the incorporation of polyoxyethylene, and the coating of pills or granules to obtain the necessary dissolution and release characteristics are time consuming and expensive manufacturing procedures. Other granular and particulate calcium channel blocker compositions formulated with a pH-dependent binding agent are known. However, the manufacture of these compositions has required the use of an organic solvent, which must subsequently be removed by arduous and lengthy drying procedures. These compositions have additionally required the application of a sustained-release or enteric coating material to obtain adequate dissolution control. There is, therefore, a need for a pharmaceutical composition which provides therapeutically effective dihydropyridine calcium channel blocker plasma levels, when administered as infrequently as twice daily, avoids the phenomenon of dose dumping, and provides readily and economically manufacturable drug-containing particles of substantially uniform and regular size and shape suitable for incorporation in hard gelatin capsules and other oral and parenteral dosage forms.

SUMMARY OF THE INVENTION

In one aspect, this invention provides a method of preparing spheroids which provide long-acting sustained release of a therapeutically effective amount of a dihydropyridine calcium channel blocker, which method consists essentially of:

(a) forming an essentially aqueous wet mass comprising an effective amount of the calcium channel blocker in admixture with a pH-dependent binder which is less soluble at lower pH and more soluble at higher pH, wherein the binder constitutes at least 3 weight percent of the dry components of the mass;

(b) extruding the wet mass to form rod-shaped, substantially cylindrical segments having diameters in the range of up to 1.2 millimeters;

(c) shaping the rod-shaped segments into spheroids; and (d) drying the spheroids.

In a second aspect, the invention provides a long acting sustained release pharmaceutical composition for administration of a therapeutically effective amount of a dihydropyridine calcium channel blocker, which comprises essentially spherical, non-coated, non-rugose particles having diameters up to 1.2 millimeters, comprised of an effective amount of calcium channel blocker in intimate admixture with at least about 3 weight percent of a pH-dependent binder which is less soluble at lower pH and more soluble at higher pH.

A further aspect of the invention provides a long acting sustained release pharmaceutical dosage form such as a capsule or injectable suspension, for administration of a therapeutically effective amount of a dihydropyridine calcium channel blocker, which dosage form consists essentially of an inert pharmaceutical carrier in which is contained:

(a) a long acting pharmaceutical composition as described above for prolonged administration of the calcium channel blocker; in combination with, (b) a fast release pharmaceutical composition for administration of a loading dose of the calcium channel blocker, wherein the relative proportions of long acting pharmaceutical composition and fast release pharmaceutical composition are in the range of 50:50 to 100:0.

Yet a further aspect of the invention is a method of treating cardiovascular disease in a mammal, which method comprises administering to a mammal in need of such treatment a therapeutically effective amount of the long acting pharmaceutical composition of this invention.

DETAILED DESCRIPTION OF THE INVENTION

Definitions

As used herein, the following terms have the meaning described below unless otherwise indicated:

The term "alkyl" refers to a straight or branched hydrocarbon chain having from one to six, preferably one to four carbon atoms. Examples of alkyl groups are methyl, ethyl, n-propyl, i-propyl, n-butyl, i-butyl, s-butyl and t-butyl.

The term "alkoxy" means a moiety of the formula —OR in which R is alkyl as defined above.

The term "alkylenyl" means a straight or branched chain bivalent alkyl bridging group.

The term "alkylenyloxyalkyl" means a moiety of the formula —R$_a$OR in which R$_a$ is alkylenyl and R is alkyl as defined above.

The term "halo" refers to chloro, bromo, iodo and fluoro. Nitro is a preferred halo substituent on the phenyl ring of the 1,4-dihydropyridyne calcium channel blockers compounds of interest in this invention.

The term "aryl" refers to homocyclic and heterocyclic moieties which are substantially aromatic in character. Examples of aryl groups are phenyl, naphthyl, imidazolyl, pyrrolyl, pyridinyl, thienyl, benzofurazanyl, benzoxadiazolyl and the like.

The term "aralkyl" refers to a alkylaryl moieties.

The terms "phenyl alkyl" and "naphthyl alkyl" mean radicals of the structure:

respectively, in which R is alkyl as defined above.

Unless otherwise indicated or defined, a chemical substituent name which consists of compound chemical group names is written in the order of appearance of the individually named groups starting with the terminus of the substituent. For example, "hydroxyalkyl" means a substituent of the formula —ROH where R is alkyl, and "alkoxyaminoalkyl" means a substituent group of the general formula —RNOR in which both R's are alkyl.

The terms "optional" and "optionally" mean that the subsequently described event or circumstance may or may not occur, and that the description includes instances where said event or circumstance occurs and instances in which it does not. For example, "optionally substituted phenyl" means that the phenyl moiety may or may not be substituted and that the description includes both substituted and unsubstituted phenyl. The phrase "optional pharmaceutical excipients" indicates that a composition or dosage form so described may or may not include pharmaceutical excipients other than those specifically stated to be present, and that the formulation or dosage form so described includes instances in which optional excipients are present and instances in which they are not.

The term "pharmaceutically acceptable acid addition salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid and the like; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

"Dihydropyridine calcium channel blocker" refers generally to any compound which contains the dihydropyridine dicarboxylic acid moiety and has calcium channel blocking activity. The compounds of formulas A and I described above in the Background of the Invention are representative of the dihydropyridine calcium channel blockers intended for use within the scope of this invention. Dihydropyridine calcium channel blockers not specifically described here may be beneficially administered from, and are included within the scope of, this invention.

"Nicardipine" identifies the compound 2,6-dimethyl-4-(3'-nitrophenyl)-1,4-dihydropyridine-3,5-dicarboxylic acid-3-methylester-5-β-(N-benzyl-N-methylamino)-ethyl ester, or any of its pharmaceutically acceptable salts. The salt, nicardipine hydrochloride, is the preferred calcium channel blocker of this invention.

The terms "treating" and "treatment" refer to any treatment of a disease in a mammal, particularly a human, and include:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The terms "fast release" and "conventional release" refer to calcium channel blocker composition that are substantially completely dissolved and absorbed in the stomach or upper gastrointestinal tract.

The terms "long acting" and "sustained release" refer to calcium channel blocker compositions that are slowly and continuously dissolved and absorbed in the stomach and gastrointestinal tract over a period of at least two hours. Preferred long acting compositions and dosage forms exhibit plasma concentration profiles suitable for twice daily administration of the dosage form.

The pharmaceutical compositions, dosage forms and methods of the invention can be used to provide long acting sustained release administration of any of the 1,4-dihydropyridine derivatives having calcium channel blocking activity. The preferred dihydropyridine calcium channel blockers of this invention are selected from the group represented by the formula:

(1)

where;
$R_1$ is $-NO_2$, $-CF_3$, or halo;
$R_2$ is alkyl or $-CH_2CH_2OCH_3$; and
$R_6$ is hydrogen or alkyl; and
$R_3$ is alkyl, alkylenyloxyalkyl, haloalkyl, optionally substituted phenyl alkyl, optionally substituted napthyl alkyl, or in which:
A is alkylene;
$R_4$ is alkyl, alkoxy, or optionally substituted phenyl or phenyl alkyl; and
$R_5$ is hydrogen or alkyl;
and the pharmaceutically acceptable salts thereof.

The long acting sustained release pharmaceutical compositions of the invention are spheroids, which are essentially spherical particles having substantially smooth, non-rugose surfaces. In contrast to conventional granules, which may be approximately spherical in their outermost surface dimensions, but are actually loose particulate aggregates with highly rugose surfaces and area radius to circumference radius ratios in the range of 0.6 to 0.8, the spheroids of this invention have area radius to circumference radius ratios in the range of 0.85 to 1.0, preferably in the range of 0.9 to 1.0. As used herein area radius is given by the formula:

the square root of [the projected area divided by pi], and the circumference radius is given by the formula:

the projected circumference divided by 2 pi.

The projected area and projected circumference including indentations or projections are determined from a projected image of the particles in question. As used herein, "non-rugose" refers to an outer surface which is substantially lacking in wrinkles, craters and other surface irregularities. The terms "spheroids" and "spherical particles" are used interchangeably herein.

Further in contrast to conventional granules, the spheroids of this invention are relatively dense. Whereas conventional granules have variable and significant degrees of porosity in the range of about 30-50% internal void volume (see for example, Chalmers A. A. and Elworthy P. H. (1976) *J. Pharm. Pharmacol.*, 28, 239-243), the spheroids of this invention have substantially decreased porosities in the range of less than about 20% internal void volume, preferably 15% internal void volume or less. The smooth surface and low porosity of the spheroids provide substantially greater dissolution control than can be achieved with conventionally manufactured granules.

The long acting sustained release pharmaceutical compositions of this invention are prepared from an essentially aqueous, wet mass containing the calcium channel blocker, pH-dependent binder, and any optional pharmaceutical excipients. The term "essentially aqueous, wet mass" refers to a powder mass which has been wetted with an essentially aqueous binding solution to a consistency suitable for extrusion. The powder mass is made by dry-blending the active ingredient(s) and any desired optional pharmaceutical excipients such as a diluent. The term "essentially aqueous" means that water is the predominant liquid in the binding solution, which may include, but preferably will not include, up to 25% other water-miscible solvents.

In the preferred embodiments of this invention, the pH-dependent binder is dissolved or dispersed in the aqueous binding solution which is used to wet the dry powder mass. However, depending on the choice of active ingredient, pH-dependent binder and other excipients, it may in some instances be preferable to include some or all of the pH-dependent binder in the dry powder mass prior to wetting with water or other essentially aqueous binding solution. Whether the pH-dependent binder is included in the dry powder mass or in the aqueous wetting solution, or both, the mixing of components which takes place to form and extrude the wet mass should be sufficient to place the active agent in intimate and substantially uniform admixture with the binder and any other excipients which may be incorporated.

In addition to, and intimately admixed with the calcium channel blocker and the pH-dependent binder in the wet mass may be other optional pharmaceutically acceptable excipients. These may include diluents such as lactose, mannitol, dry starch, microcrystalline cellulose and the like, additional binders such as starch, gelatin, sugars, carboxymethylcellulose, methylcellulose and the like, lubricants such as talc and magnesium stearate, coloring agents and flavoring agents.

The wet mass is then extruded to form rod-shaped, substantially cylindrical segments having diameters in the range of up to 1.2 millimeters. As used herein, the term "extrusion" refers to a process whereby a cohesive rod-shaped, substantially cylindrical material of specific cross section is formed by forcing the wet mass, from a wide diameter reservoir, through an orifice of small diameter, such that the product substantially retains the cross section of the orifice. These rod-shaped segments can then be formed into spheres, as described below, and it is therefore important that they be substantially cylindrical and of relatively uniform cross section. The extrusion step should also impart additional density (low porosity) to the material, which may be further densified during the spheronization step.

There are a wide variety of such extrusion methods known and available in the pharmaceutical industry. In general, these methods rely on generation of a continuous pressure of sufficient magnitude to induce the material to flow and retain the shape of the die on exit. The degree of wetness, flow and cohesive properties of the wet mass also affect the quality and uniformity of the extruded material. Well known, standard types of extrusion equipment suitable for use in this invention include screw extruders, cylinder extruders, gear extruders, ram extruders and radial screen rotating head type extruders.

The extruded rod-shaped segments are then shaped into spherical particles, which when dry, are long acting sustained release spheroids suitable for use in a variety of oral and parenteral dosage forms. As discussed above, in order to provide the desired prolonged dissolution and release profiles, the outer surface of the spheroids must be substantially smooth, non-rugose and essentially spherical. Spheronization equipment capable of forming spheroids having the desired properties from cylindrical extrudate is commercially available. For example, the Marumerizer machine (Conine J. W. and Hadley H. R. (1970) Drug Cosmet. Ind., 106, 38–41) can be used to provide spherical particles of suitable surface smoothness and regularity of size and shape. In the Marumerizer, the rod-shaped segments of extrudate are shaped into spheroids by centrifugal and frictional forces on a rotating disc or pan. This method of spheronization offers the opportunity to regulate the size of the spherical particles.

The spheroids may be varied in size up to about 1.2 mm, and the size of the spheroids can be adjusted to control the rate of spheroid dissolution and drug release. Smaller spheroids have higher surface to volume ratios, and hence faster dissolution rates, than larger spheroids. The preferred size for spheroids is between about 0.5 mm and 1.2 mm, most preferably between about 0.7 mm and 1.0 mm. It is also preferred that the size distribution of the spheroids be as narrow as possible; spheroids within a narrow size distribution range provide a plasma concentration profile which is more flat and constant than that achieved with particles of widely differing sizes. In the preferred embodiments of this invention at least 70 weight percent of the spheroids will have diameters which are within upper and lower limits differing by not more than a factor of the square root of two from each other.

In order to provide sustained release of the dihydropyridine calcium channel blocker, the binder materials suitable for use in this invention must control the dissolution profile of the drug-containing spheroids so that they dissolve slowly and continuously throughout their passage within the stomach and along the gastrointestinal tract. The dissolution control capacity of the binding agent is particularly important in a long-acting dosage form; a sustained release dosage form which contains sufficient drug for once or twice daily adminstration may cause untoward side effects if it dissolves too rapidly and dumps all of the drug into the stomach and upper gastrointestinal tract in a short period of time.

Accordingly, binders suitable for use in this invention are materials which prevent rapid dissolution of the spheroids during their residence in the very acidic environment of the stomach (where the pH is generally less than about 4.5) and prolong the dissolution of the spheroids in the intestinal tract (where the pH is generally greater than about 5.5). Any material which is pharmaceutically acceptable for oral ingestion and which can impart such dissolution control to the calcium channel blocker spheroids can be used in this invention. Generally these materials are substantially insoluble at a pH of less than about 4.5 and are soluble at a pH of greater than 5.5. Many materials known in the pharmaceutical art as "enteric" binders and coating agents have the desired properties. These include a large number of phthalic acid derivatives such as the phthalic acid derivatives of vinyl polymers and copolymers, hydroxyalkylcelluloses, alkylcelluloses, cellulose acetates, hydroxyalkylcellulose acetates, cellulose ethers, alkylcellulose acetates, and the partial esters thereof; and polymers and copolymers of lower alkyl acrylic acids and lower alkyl acrylates, and the partial esters thereof.

Examples of specific pH-dependent binder materials which may be used include hydroxypropyl cellulose phthalate, cellulose acetate phthalate, polyvinylacetate phthalate, polyvinylpyrrolidone phthalate, hydroxypropylmethyl cellulose phthalate and copolymers of methacrylic acid and methacrylic or acrylic acid esters. Particularly preferred binders for use in this invention are the commercially available copolymers of methacrylic acid and a methacrylic or acrylic acid ester, for example the Eudragit polymers, particularly the Eudragit L series such as Eudragit L30D and Eudragit L100/55, sold by the Rohm and Haas Company. Eudragit L30D is a dispersion of 30% Eudragit L powder in water, and is the preferred pH dependent binder for use in this invention. It is to be noted that viscosity enhancing agents such as hydroxypropylmethylcellulose, methylcellulose and polyvinylpyrrolidone which dissolve at a rate independent of pH, do not provide the required dissolution control.

The spheroids may contain the calcium channel blocker in any proportion from as little as 1 weight percent or less up to about 95 weight percent. The pH-dependent binder may be present in any proportion from as little as 3 weight percent up to about 95 weight percent. While the proportion of active agent present will depend largely on its potency, the proportion of pH-dependent binder will depend on the degree of release rate control which is needed for the particular active agent. Generally, the pH-dependent binder will constitute about 5 to 50 weight percent, preferably about 5 to 25 weight percent of each spherical particle. A preferred spheroid composition for the administration of nicardipine hydrochloride will contain about 10 to 25 weight percent nicardipine and about 5 to 25 weight percent pH-dependent binder, with the remainder being non-essential fillers, binders and other optional excipients. A particularly preferred spheroid composition for the administration of nicardipine hydrochloride is:

| ingredient | weight % |
| --- | --- |
| nicardipine HCL | 20 |
| microcrystalline cellulose | 20 |
| maize starch | 20 |
| lactose | 29 |
| Eudragit L | 11 |

Because the spheroids are not coated, and do not contain central seeds or cores, if an error has been made in the preparation of the wet mass, extrudate, or spheroids, the incorrectly formed material can readily be reworked and reformed.

Utility and Administration

Depending on the particular calcium channel blocker which is incorporated, the pharmaceutical compositions and dosage forms of the invention may be used for treating a wide variety of disease states which involve one or more forms of cardiovascular and cerebrovascular dysfunction. The calcium channel blockers of interest in the invention generally possess a broad spectrum of cardiovascular and cerebrovascular activities including anti-anginal and antihypertensive properties. Nicardipine also possesses anti-ischemic properties. The invention compositions can therefore be beneficially used in treating cardiovascular and cerebrovascular disorders in patients who are susceptible to calcium ion entry blockade.

The preferred method of administration of these compositions is oral, except in those cases where the patient is unable to ingest, by himself, medication. In such instances it may be necessary or desirable to administer the composition parenterally. The preferred oral dosage forms of the invention are capsules, preferably hard gelatin capsules, which contain the long acting spheroids in amounts suitable for the desired dosage period. Other dosage forms for oral administration include powders or spherical particulates for ingestion with foods or beverages.

Because the spherical particles of the invention exhibit a prolonged release profile in physiological environments of pH 4 to 7, they can also be formulated in parenteral suspensions or slow release depot formulations for subcutaneous or intramuscular injection. The parenteral dosage forms can be prepared by suspending the spheroids and optional pharmaceutical adjuvants in a carrier, such as, for example, water, saline solutions, aqueous dextrose, glycerol and the like. The dosage form may also contain minor but effective amounts of non-toxic auxiliary substances such as wetting and emulsifying agents, pH buffering agents and the like, for example, sodium acetate, sorbitan monolaurate, triethanolamine sodium acetate, triethanolamine oleate and the like. Actual methods of preparing such dosage forms are known, or will be apparent to those skilled in this art; for example, see *Remington's Pharmaceutical Sciences*, Mack Publishing Company, Easton, Pa., 15th Edition, 1975.

Depending on the intended therapeutic application of the calcium channel blocker, it may be desirable to administer a loading dose of a fast-release calcium channel blocker composition (i.e. a composition that is substantially completely dissolved and absorbed in the stomach and upper gastrointestinal tract) in conjunction with a long acting sustained release composition. The long-acting spheroids of this invention can be readily formulated in a pharmaceutical dosage form, such as a hard gelatin capsule, which also contains a fast release composition for administration of a loading dose of the calcium channel blocker. Where a fast release loading dose is desired, the relative proportions of long acting pharmaceutical composition and fast release pharmaceutical composition should preferably be in the range of 50:50 to 100:0, most preferably in the range of 60:40 to 80:20. The fast release composition may simply be additional quantities of the dry powder mass used to form the spheroids, and may contain optional pharmaceutical excipients. Alternatively, it can be a granulated or spherical particulate, or any other physical form which incorporates the drug in an inert non-sustained release pharmaceutical carrier material.

In a long acting capsule dosage form, the void spaces between the essentially spherical particles may be filled with a fast release calcium channel blocker powder composition. The long acting capsule dosage form would then possess the combined release properties of the fast release and long acting compositions. The overall release rate profile of the dosage form can be controlled by varying the ratios of the fast release portion and the long acting portions of the final preparation.

When the capsule is ingested, the fast release portion provides a loading dose while the contents of the capsule are in the stomach. As the contents of the capsule move into the intestine, the long acting spheroids continue to dissolve, providing release of calcium channel blocker over at least two hours, preferably over at least four to eight hours. The blood plasma levels approach therapeutic levels rapidly and remain at therapeutic levels for an extended period of time.

In addition to providing ease and economy of manufacture, the compositions and dosage forms of the present invention provide several therapeutic advantages. Because of the long-acting properties of the spheroids, the pharmaceutical compositions and dosage forms of the invention can be designed to provide therapeutic calcium channel blocker plasma concentration profiles suitable for twice daily administration. In measurements of drug plasma concentration versus time, the long acting compositions of the invention provide therapeutic plasma concentrations for a period at least about twice that which is provided by a conventional fast release formulation. Embodiments of the invention which combine a fast release composition with a long acting composition also exhibit greatly enhanced drug plasma profiles suitable for twice daily adminstration.

EXAMPLES

The following examples are exemplary of the invention described in the specification and claims. They are not to be construed as limiting the scope of the claims.

Example 1

Preparation of Long Acting Spheroids

A. 1.0 Kg nicardipine hydrochloride, 1.2 Kg lactose monohydrate, 1.0 Kg Avicel PH 102, and 1.0 Kg maize starch were blended for 20 minutes in a Hobart mixer. A mixture of 2.4 Kg of Eudragit L30D (brand copolymer of methacrylic acid and acrylic acid ethyl ester, a 30% dispersion of Eudragit L in water), and 1.4 Kg of distilled water were added to the dry mixture and the wet mass mixed for 5 minutes in a Hobart mixer. The wet mass was then extruded through an Elanco extruder having a screen size of 1 mm, giving substantially cylindrical rod-shaped segments approximately 1 mm in diameter. The rod-shaped segments were placed into a GB Caleva Model 15 spheronizer having a plate that rotated at about 800 revolutions per minute for 5 minutes. The spheronized particles were then dried in an oven at 50° C. for 180 minutes. (The residence time in the spheronizer is variable for any batch of particles, and varies from 3 to 10 minutes).

B. In like manner, long acting sustained release spheroids may be prepared from other dihydropyridine calcium channel blocker including nifedipine, niludipine, nitrendipine, nisoldipine, nimodipine, and felodipine.

Example 2

Preparation of Fast Release Powder

A. 1.0 Kg nicardipine hydrochloride and 3.975 Kg pregelatinized starch were blended for 20 minutes in a Hobart mixer. 0.025 Kg of magnesium stearate was then added and blended for 3 minutes. This powder was then used as a fast release composition in the capsules described in Example 3.

B. In like manner, fast release powder compositions may be prepared from other dihydropyridine calcium channel blocker including nifedipine, niludipine, nitrendipine, nisoldipine, nimodipine, and felodipine.

Example 3

Preparation of Long Acting Dosage Form Containing Fast Release Loading Dose

Hard gelatin capsules were filled with a mixture of the dried and sized nicardipine spheroids of Example 1.A. and the fast release nicardipine powder of Example 2.A., in the relative proportions of 50 weight percent and 50 weight percent, respectively.

Example 4

This example shows the dissolution rates in a standard USP paddle test of a fast release nicardipine composition prepared as described in Example 2, two long acting spheroid compositions prepared accordingly to the procedure described in Example I, and two compositions combining long acting spheroids with fast release powder.

TABLE 1

AMOUNT OF NICARDIPINE DISSOLVED (PERCENTAGE)

| Time (mins.) | Fast Release Powder (30 mg) | Long Acting Spheroids with 14.4% Eudragit L (30 mg) | Long Acting Spheroids with 14.4% Eudragit L (30 mg) and Fast Release Powder (30 mg) | Long Acting Spheroids with 7.2% Eudragit L (30 mg) | Long Acting Spheroids with 7.2% Eudragit L (30 mg) and Fast Release Powder (30 mg) |
| --- | --- | --- | --- | --- | --- |
| 5 | 23 | | | | |
| 10 | 82 | | | | |
| 15 | 89 | 9 | 46 | 16 | 48 |
| 30 | 99 | 17 | 54 | 24 | 57 |
| 45 | 99 | 21 | 57 | 29 | 60 |
| 60 | 99 | 23 | 59 | 32 | 61 |
| 90 | | 27 | 61 | 38 | 64 |
| 120 | | 30 | 63 | 43 | 66 |
| 180 | | 33 | 66 | 48 | 69 |
| 240 | | 36 | 67 | 51 | 70 |

A standard USP paddle dissolution test was run at 50 RPM in 1000 ml of pH 4.5 citrate buffer solution containing samples of the formulations to be tested. The two long acting spheroid compositions were made by varying the amounts of Eudragit L (expressed in % dry weight of the spheroid components). The fast release composition and the long acting composition were combined as in Example 3 to give 30 mg nicardipine hydrochloride in the fast release composition and 30 mg nicardipine hydrochloride in the long acting spheroids.

Dissolution rate results for each composition and combination tested are given in Table 1. The results show that the fast release component is completely dissolved in about 30 minutes. The two long acting compositions exhibit much slower and more prolonged dissolution profiles.

Example 5

In this example the post administration drug plasma concentrations of three dosage forms, one a conventional fast release capsule, and the two others long acting dosage forms prepared according to this invention, are compared. The fast acting dosage form (Dosage Form A) was a fast release powder prepared as described in Example 2 and placed in single dose capsules, each containing 30 mg of nicardipine hydrochloride. The long acting dosage forms were also capsules, each containing 30 mg nicardipine hydrochloride in the fast release powder composition and 30 mg nicardipine hydrochloride in long acting spheroid compositions having either 14.4% (Dosage Form B) or 7.2% Eudragit L (Dosage Form C). The testing was conducted in five human volunteers in a three-way balanced crossover test, comparing the two long acting formulations with the fast release formulation.

Plasma samples were removed and tested by gas chromatography for nicardipine at intervals. The results are tabulated in Table 2 as plasma levels observed at a given time after dosage administration.

Figure 1:
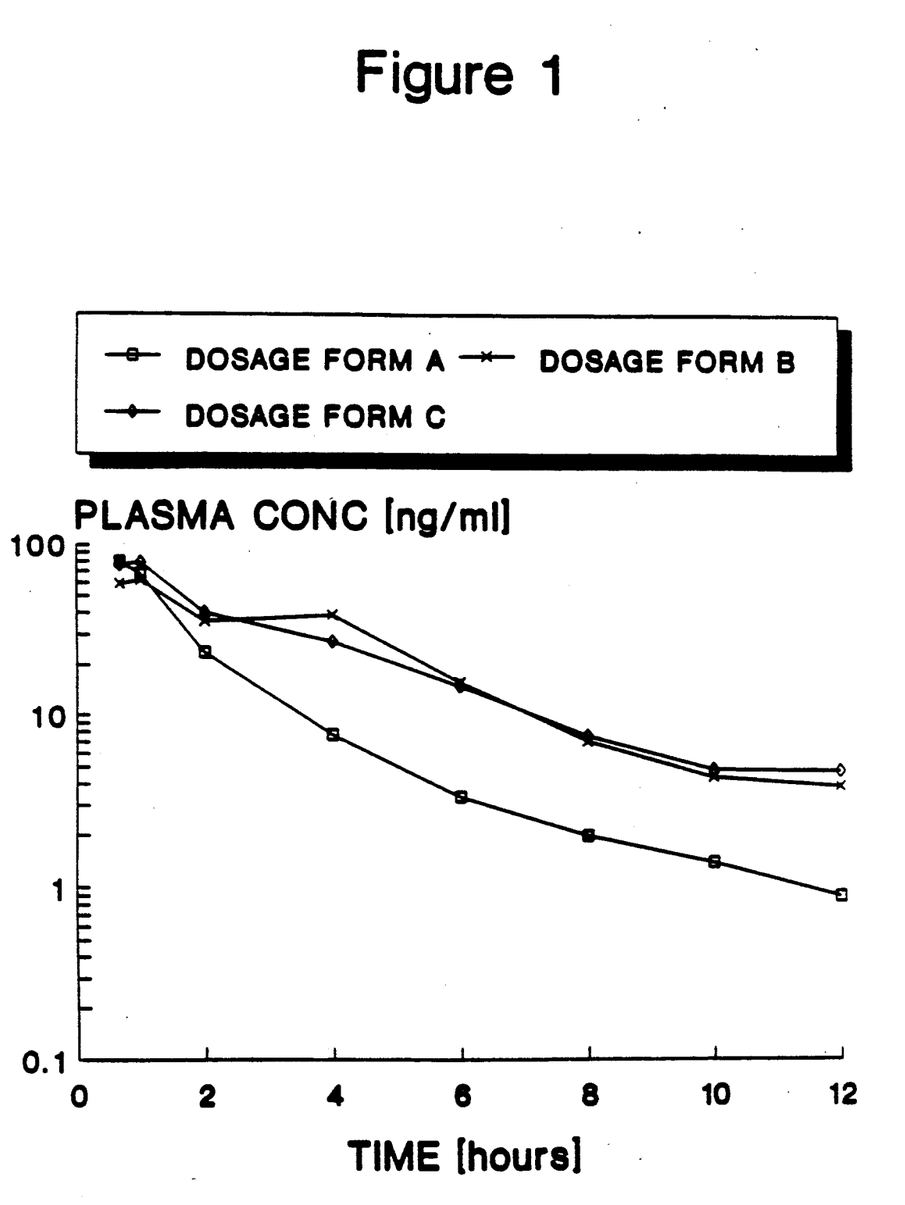
FIG. 1 is a graphical presentation of the results of the test described in Example 5 and shows comparative plasma concentration profiles of nicardipine hydrochloride achieved after administration of a conventional fast acting dosage form (Dosage Form A) and two long acting dosage forms prepared according to the present invention (Dosage Forms B and C).

A comparison of the pharmacokinetic parameters of the formulations of Table 2 are shown in Table 3. FIG. 1 graphically depicts the data set forth in Table 2 and shows the profiles of mean plasma nicardipine level versus time achieved with each of Dosage Forms A, B and C.

TABLE 2

NICARDIPINE HCl PLASMA LEVELS IN HUMANS
(ng/ml) (Mean of five subjects)

| Time (hour) After Administration | Dosage Form A (30 mg dose) | Dosage Form B (60 mg dose) | Dosage Form C (60 mg dose) |
| --- | --- | --- | --- |
| 0.67 | 79.9 | 59.3 | 76.5 |
| 1.0 | 67.5 | 62.3 | 79.6 |
| 2.0 | 23.7 | 35.8 | 40.2 |
| 4.0 | 7.7 | 39.0 | 27.4 |
| 6.0 | 3.4 | 15.9 | 15.0 |
| 8.0 | 2.0 | 7.1 | 7.6 |
| 10.0 | 1.4 | 4.4 | 4.9 |
| 12.0 | 0.9 | 3.9 | 4.8 |

TABLE 3

SUMMARIZED PHARMOKINETIC DATA

| DOSAGE FORM | DOSE (mg) | $C_{max}$ | TOTAL AUC |
| --- | --- | --- | --- |
| A | 30 | 79.9 | 131 |
| B | 60 | 68.7 | 250 |
| C | 60 | 81.1 | 247 |

For each of the three dosage forms, Table 3 shows the maximum nicardipine plasma concentration ($C_{max}$) in ng/ml and the total area under the plasma concentration/time curve (Total AUC) in ng.hr/ml. The data recorded in Tables 2 and 3 show that the long acting compositions do not dump the calcium channel blocker dose, nor release it as quickly as the conventional fast release formulation. Substantially higher Total AUC values were exhibited by the long acting compositions, indicating the prolonged maintenance of plasma levels. Three to five fold higher plasma concentrations after four hours were also exhibited by the two long acting compositions.

Example 6

Preparation of Long Acting Dosage Form

Hard gelatin capsules were filled with nicardipine spheroids prepared according to the method described in Example 1 with sufficient Eudragit L30D to give a final composition containing 11 weight % Eudragit L. Each capsule contained 60 mg of nicardipine hydrochloride in the long acting spheroid composition only.

Example 7

In this example the post administration drug plasma concentrations of two dosage forms, one a conventional fast release capsule and the other a long acting dosage form, prepared according to this invention are compared.

The fast acting dosage form was a fast release powder prepared as described in Example 2 and placed in a single dose capsule containing 30 mg of nicardipine hydrochloride. The long acting dosage form was also a capsule, containing 60 mg of nicardipine hydrochloride in the long acting spheroid compositions described in Example 6.

The testing was carried out in five human volunteers in a two-way balanced crossover study. Plasma samples were removed and tested by gas chromatography for nicardipine at intervals. The results are tabulated in Table 4 as plasma levels observed at a given time after dosage administration.

Figure 2:
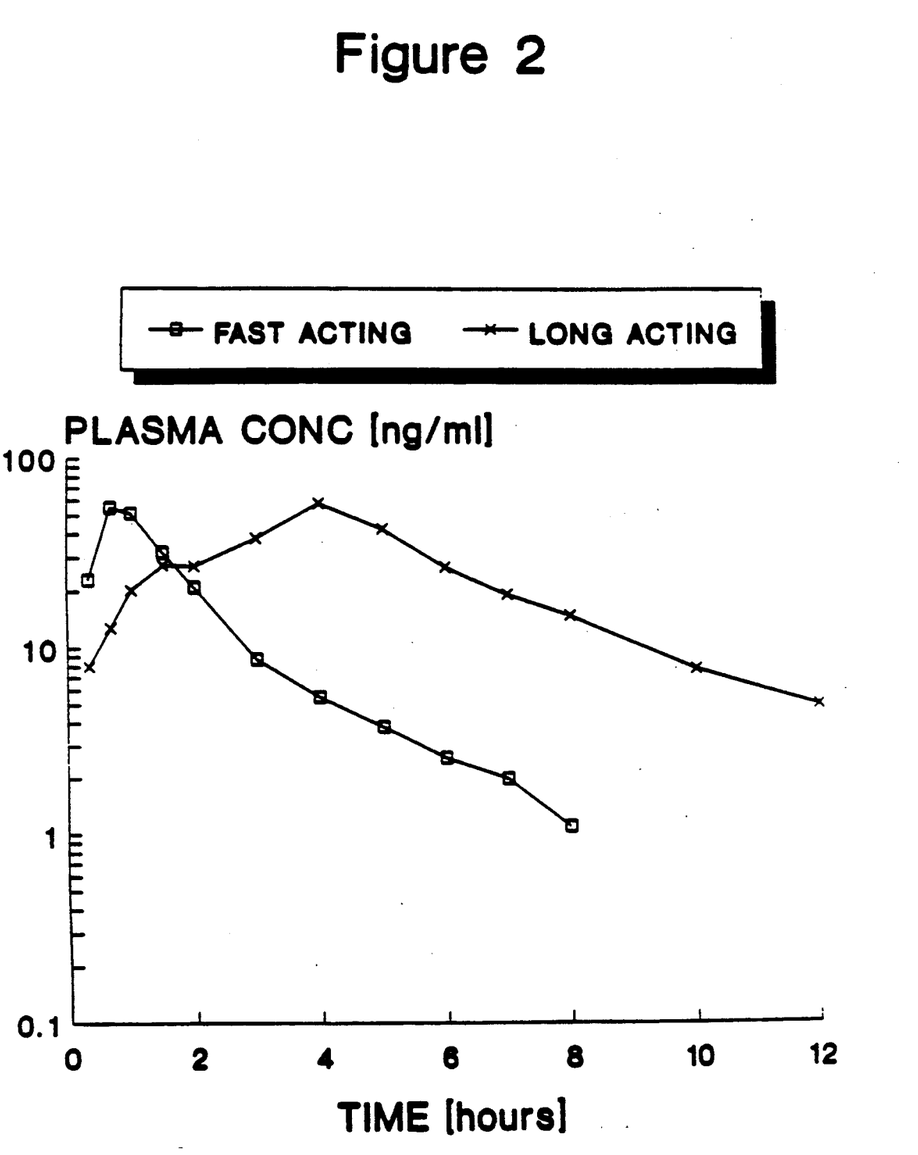
FIG. 2 is a graphical presentation of the results of the test described in Example 7 and shows the comparative plasma concentration profiles of nicardipine hydrochloride achieved after administration of a conventional fast acting dosage form and a long acting dosage form prepared in accordance with this invention.

A comparison of the pharmacokinetic parameters are shown in Table 5. FIG. 2 graphically depicts the data set forth in Table 4, and shows the profiles of mean plasma nicardipine concentration level versus time achieved with the fast acting and long acting dosage forms.

TABLE 4

| Nicardipine Hydrochloride Plasma Levels in Humans (ng/ml) (mean of five subjects) | | |
| --- | --- | --- |
| Time (hour) After Administration | Fast Acting (30 mg Dose) | Long Acting (60 mg Dose) |
| 0.33 | 23.0 | 8.0 |
| 0.66 | 55.0 | 12.8 |
| 1.0 | 51.5 | 20.3 |
| 1.5 | 32.1 | 27.5 |
| 2 | 21.0 | 27.2 |
| 3 | 8.7 | 37.8 |
| 4 | 5.5 | 57.7 |
| 5 | 3.8 | 42.3 |
| 6 | 2.6 | 26.7 |
| 7 | 2.0 | 19.2 |
| 8 | 1.1 | 14.8 |
| 10 | bg | 7.7 |
| 12 | bg | 5.0 | bg denotes levels of less than 1 ng/ml

TABLE 5

| | Summarized Pharmacokinetic Data | | | |
| --- | --- | --- | --- | --- |
| Dosage Form | Dose (mg) | $T_{max}$ (hours) | $C_{max}$ (ng/ml) | Total AUC (ng · hr/ml) |
| Fast Acting | 30 | 0.8 | 68.1 | 105 |
| Long Acting | 60 | 3.6 | 63.0 | 277 |

For both dosage forms, Table 5 shows the time after administration at which maximum nicardipine plasma concentration occurred concentration occurred ($T_{max}$) in hours, the maximum nicardipine plasma concentration ($C_{max}$) in ng/ml and the total area under the plasma concentration/time curve (Total AUC) in ng.hr/ml.

The data recorded in Tables 4 and 5 show that the long acting composition does not dump the calcium channel blocker dose, nor release it as quickly as the conventional fast release formulation. Substantially higher $T_{max}$ and Total AUC values were exhibited by the long acting composition, indicating the prolonged maintenance of plasma levels. Five to ten fold higher plasma concentrations were exhibited by the long acting composition at sampling times of 4 hours and longer after dosage administration.

Example 8

Preparation of Long Acting Dosage Form Containing a Fast Release Loading Dose Hard gelatin capsules were filled with a combination of nicardipine spheroids prepared according to the method set forth in Example 1 containing 11% Eudragit L, and the fast release nicardipine powder of Example 2, in the relative proportions of 75 weight percent and 25 weight percent respectively. The capsules contained 45 mg or 60 mg of nicardipine hydrochloride, distributed in the fast release and long acting compositions in the amounts shown in Table 6.

TABLE 6

| | Total | Nicardipine Dose (mg) as | |
| --- | --- | --- | --- |
| Dosage Form | Nicardipine Dose (mg) | Fast Release Powder | Long Acting Spheroids |
| A | 45 | 11.25 | 33.75 |
| B | 60 | 15.45 | 45.00 |

Example 9

In this example the post administration drug plasma concentration profiles achieved with three dosage forms, one a conventional fast release capsule and the two others long acting dosage forms prepared according to this invention, are compared.

The fast acting dosage form (Dosage Form A) was a fast release powder prepared as described in Example 2, and placed in single dose capsules each containing 30 mg of nicardipine hydrochloride. The long acting dosage forms (Dosage forms B and C) were also capsules each containing fast release powder and long acting spheroid nicardipine hydrochloride compositions in the relative proportions of 25 weight percent and 75 weight percent respectively.

Two different nicardipine hydrochloride doses were evaluated in the long acting dosage forms. Dosage Form B contained a total of 45 mg of nicardipine hydrochloride, and Dosage Form C a total of 60 mg of nicardipine hydrochloride, each in the relative amounts set forth in Example 8.

The testing was conducted in six human volunteers in a three-way balanced crossover study, comparing the two long acting dosage forms with the fast release dosage form. Plasma samples were removed and tested by gas chromatography for nicardipine at intervals. The results are tabulated in Table 7 as plasma levels observed at a given time after dosage administration.

Figure 3:
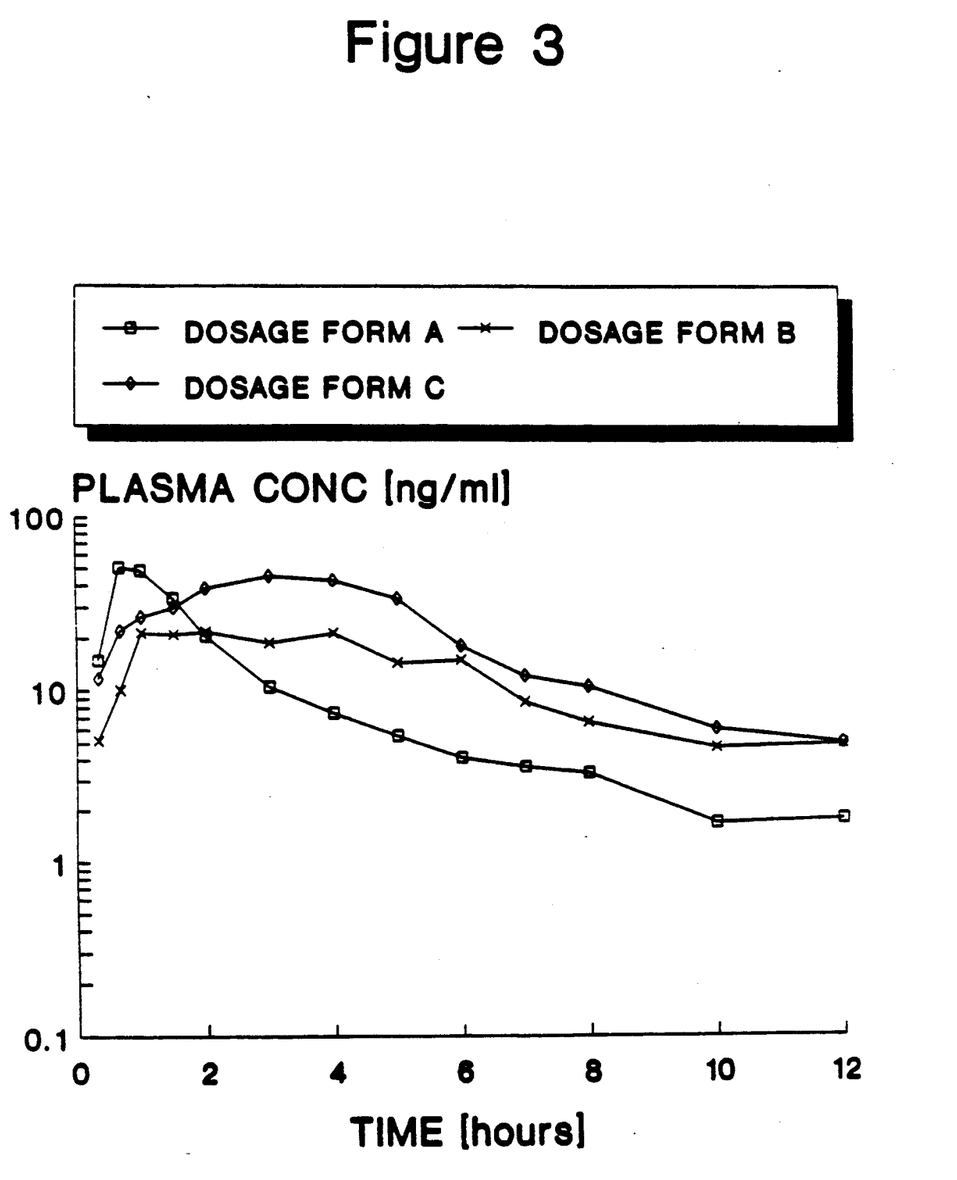
FIG. 3 is a graphical presentation of the results of the test described in Example 9 and shows the comparative plasma concentration profiles of nicardipine hydrochloride achieved after administration of a conventional fast acting dosage form (Dosage Form A) and two long acting dosage forms prepared according to this invention (Dosage Forms B and C).

A comparison of the pharmacokinetic parameters are shown in Table 8. FIG. 3 graphically depicts the data set forth in Table 7, and shows the profiles of mean plasma nicardipine concentration versus time achieved with each of Dosage forms A, B and C.

TABLE 7

Nicardipine Hydrochloride Plasma Levels in Humans (ng/ml) (Mean of Six subjects)

| Time (hours) After Administration | Dosage Form A | Dosage Form B | Dosage Form C |
|---|---|---|---|
| 0.33 | 14.9 | 5.2 | 11.7 |
| 0.67 | 50.7 | 10.1 | 22.1 |
| 1 | 48.7 | 21.6 | 26.6 |
| 1.5 | 33.9 | 21.1 | 30.0 |
| 2 | 20.8 | 22.0 | 38.8 |
| 3 | 10.5 | 19.0 | 45.4 |
| 4 | 7.0 | 21.5 | 43.1 |
| 5 | 5.6 | 14.5 | 33.9 |
| 6 | 4.2 | 15.1 | 18.2 |
| 7 | 3.7 | 8.7 | 12.2 |
| 8 | 3.4 | 6.7 | 10.6 |
| 10 | 1.7 | 4.8 | 6.1 |
| 12 | 1.8 | 5.0 | 5.1 |

TABLE 8

Summarized Pharmacokinetic Data

| Dosage Form | Dose (mg) | $T_{max}$ | $C_{max}$ | Total AUC |
|---|---|---|---|---|
| A | 30 | 0.84 | 54.6 | 117 |
| B | 45 | 2.0 | 30.2 | 145 |
| C | 60 | 3.7 | 58.7 | 254 |

For each of the three dosage forms, Table 8, shows the time after administration at which maximum nicardipine plasma concentration occurred ($T_{max}$) in hours, the maximum nicardipine plasma concentration ($C_{max}$) in ng/ml and the total area under the plasma concentration/time curve (Total AUC) in ng.hr/ml.

The data recorded in Tables 7 and 8 show that the long acting compositions do not dump the calcium channel blocker does, nor release it as quickly as the conventional fast release formulation. Substantially higher $T_{max}$ and increased Total AUC values were exhibited by the long acting formulations indicating prolonged maintenance of plasma levels.

The 45 mg nicardipine hydrochloride long acting dosage form exhibited two to five fold higher plasma levels after four hours post dosage administration than the conventional fast release dosage form. Three to six fold higher plasma levels after four hours post dosage administration were exhibited by the 60 mg nicardipine hydrochloride long acting formulation.

Both long acting formulations showed similarily enhanced and extended overall plasma concentration/time profiles, evidence by extended $T_{max}$ values with elevated plasma levels at longer sampling times. The plasma levels and Total AUC values obtained were greater for the 60 mg long acting dosage form than for the 45 mg long acting dosage form.

Example 10

Determination of Particles Surface Characteristics

The degree of rugosity of the surfaces of long acting spheroids and conventional granules were determined and compared as follows.

Long acting nicardipine hydrochloride spheroids were prepared as described in Example 1 with enough Eudragit L30D to give a final product containing 11% Eudragit L. Some of the spheroids were rotated in the spheronizer (spheronized) for one minute and some were rotated for three minutes. Conventional granules containing nicardipine hydrochloride were prepared as follows: 1.0 Kg nicardipine hydrochloride, 1.45 Kg lactose, 1 Kg Avicel PH 102, and 1 Kg maize starch were blended for 20 minutes in a Hobart Mixer. A mixture of 1.833 Kg Eudragit L30D and 0.5 Kg of distilled water were added to the dry mixture. The wet mass was then screened through an oscillating granulator having a screen size of 1 mm. The granules were then dried in an oven at 50° C., resulting in dry granules containing approximately 11% Eudragit L.

Samples of the spheroids and granules were viewed and their outline traced on paper under a microscope at ×50 magnification. The "circumference", or distance around the periphery of each spheroid or granule, was determined using a map measuring pen (Jakar, Sime and Malloch Ltd., Edingburgh, Scotland). The area within the circumference was determined by carefully cutting out the traced circumferential shape, accurately weighing the cut-out using a Cahn Microbalance, and calculating the actual area by reference to a sample of known area.

The rugosity parameter (degree of rugosity) was determined as a function of the area radius and the circumference radius from the following radius estimations:

$$\text{area radius} = R_A = \sqrt{\frac{\text{area}}{\pi}}$$

$$\text{circumference radius} = R_C = \frac{\text{circumference}}{2\pi}$$

The ratio $R_A/R_C$ is thus a measure and function of the shape (1.0 for perfect sphere) and of the surface roughness. The means values determined for the spheroids and granules are shown below.

| Sample | $R_A/R_C$ Ratio |
|---|---|
| Granules | 0.7171 +/− 0.083 |
| Spheroids (1 min. sph*) | 0.9219 +/− 0.041 |
| Spheroids (3 min. sph) | 0.9979 +/− 0.037 |

*spheronization time

Example 11

Comparison of Dissolution Behavior of Enteric granules and Long Acting Spheroids Granules containing 14.4% Eudragit L and 20 weight % nicardipine HCL were manufactured by conventional granulation techniques and their dissolution characteristics were compared with long acting spheroids of the same composition.

A. Manufacture of Enteric Granules and Long Acting Spheroids

Enteric granules containing nicardipine hydrochloride were prepared as follows: 1.0 Kg nicardipine HCL, 1.28 Kg lactose, 1.0 Kg microcrystalline cellulose and 1.0 kg maize starch were blended for 30 minutes in a Hobart Mixer. A mixture of 2.4 Kg Eudragit L30D and 0.25 Kg distilled water were added to the dry mixture. The resulting wet mass was then screened through an oscillating granulator having a screen size of 1 mm. The granules were then dried in an oven at 50° C., resulting in dry granules containing 14.4 weight % Eudragit L.

Long acting spheroids were prepared having the same composition as the enteric granules but manufactured by the extrusion spheronization method described in Example 1.

B. Dissolution Behavior Comparison

Figure 4:
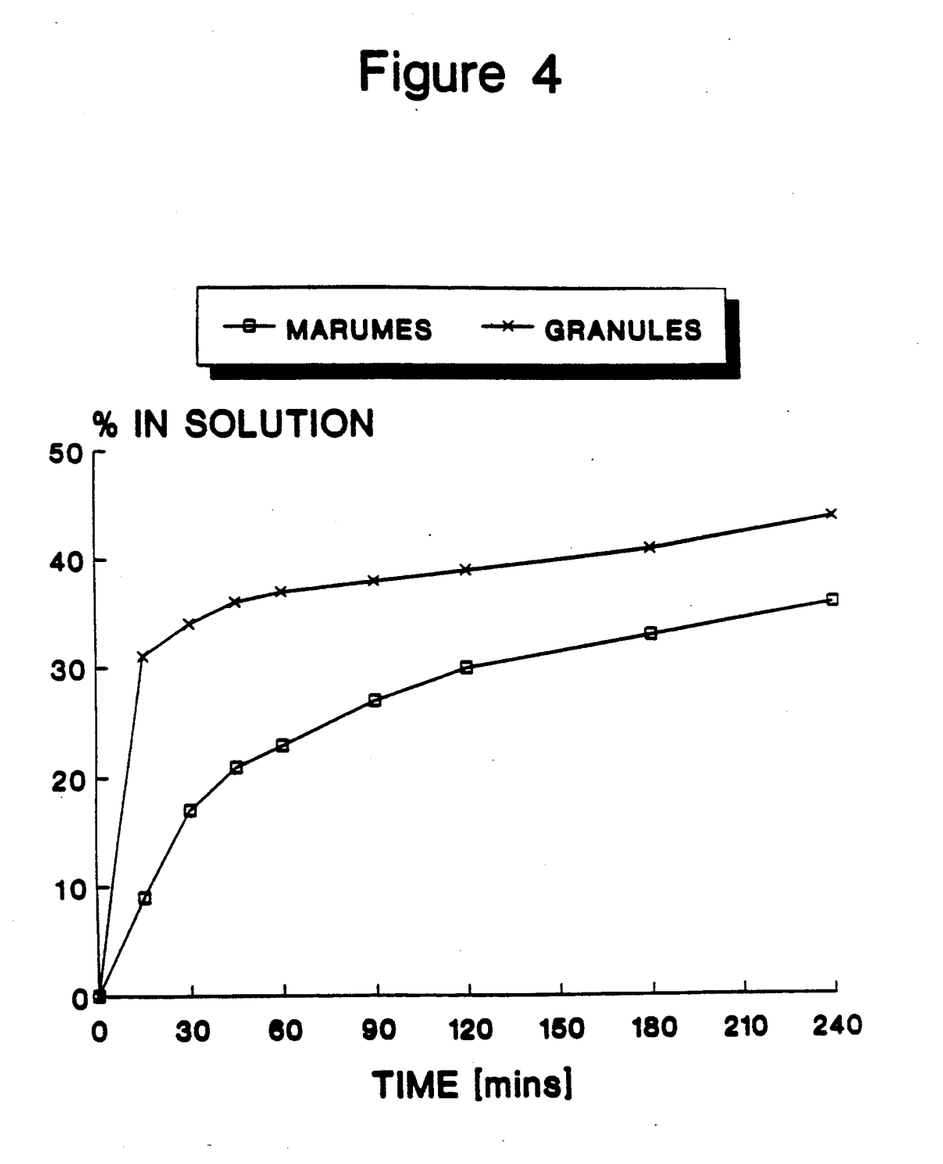
FIG. 4 is a graphical presentation of the results of the test described in Example 11 and shows the comparative dissolution behaviour in a standard USP paddle test at 50 rpm fixed paddle, 100 ml citrate at pH 4.5 of long acting spheroids prepared according to this invention and conventional granules of the same composition.
Figure 5:
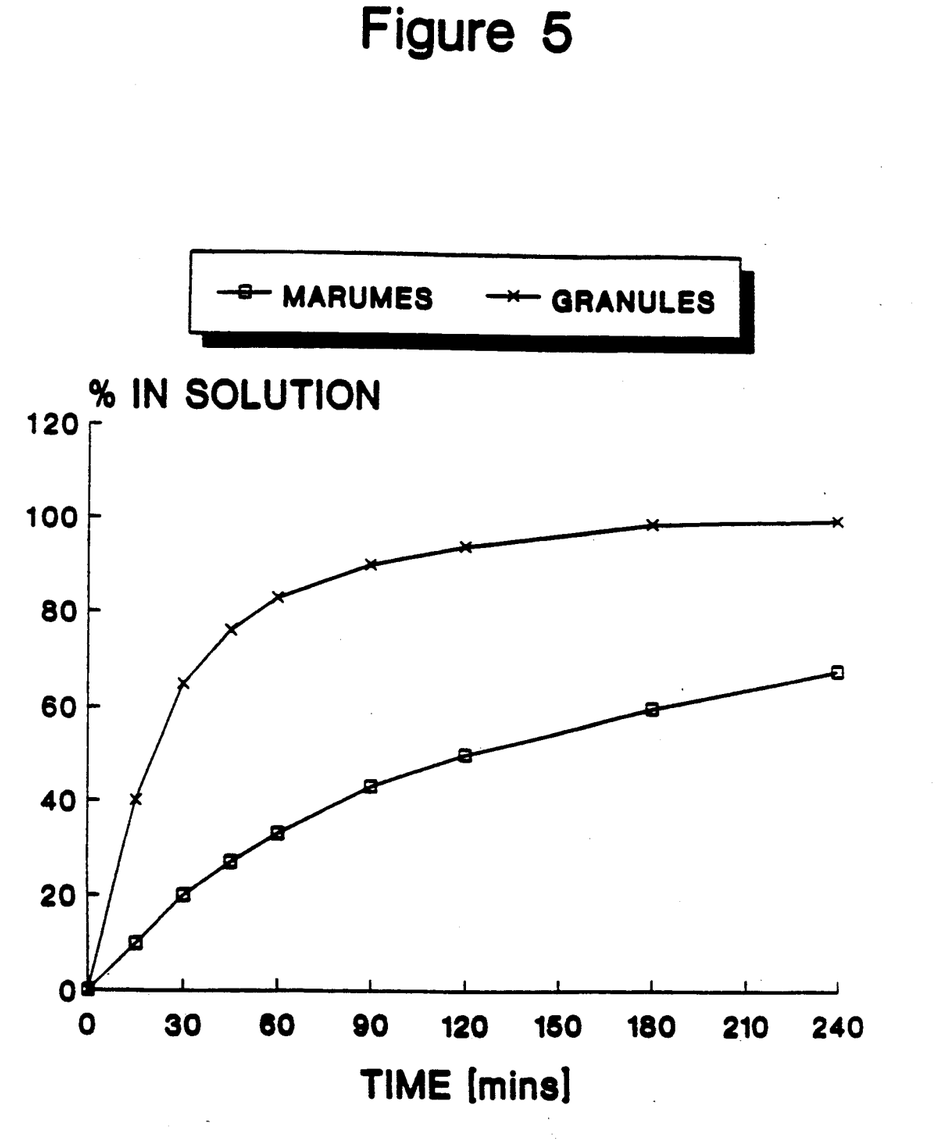
FIG. 5 is a graphical presentation of the results of the test described in Example 11 and shows the comparative dissolution behaviour in a standard USP paddle test at pH 1 of long acting spheroids prepared according to this invention and conventional granules of the same composition.

Two standard USP paddle dissolution tests were run at 50 RPM in 1000 ml of citrate buffer solution (pH 4.5) and in 1000 ml of 0.1N HCL (pH 1). Results comparing the granules and spheroids are detailed in FIGS. 4 and 5. The dissolution rate of the granules is at least twice that of the long acting spheroids at pH 1 and was substantially faster than the spheroids at pH 4.5. The decrease in dissolution rate shown by the spheroids is particularly marked during the first half of the dissolution tests, when the majority of the granule dissolution takes place.

Visual examination of the spheroids and granules during the dissolution tests showed intact spheroids with only uniform surface erosion visible at the end of 8 hours at both pH 1 and pH 4.5. In contrast, the granules showed much more rapid and variable disintegration, with essentially no granules remaining after 8 hours at pH 1, and variably sized non-uniform aggregates of particles remaining after 8 hours at pH 4.5.

What is claimed is:

1. A long acting sustained release pharmaceutical composition for administration of a therapeutically effective amount of non-amorphous nicardipine hydrochloride, which comprises essentially spherical, non-coated, non-rugose particles having diameters of about 0.5 millimeters to 1.2 millimeters, comprised of about 10 to 25 weight percent of said non-amorphous nicardipine hydrochloride in intimate admixture with about 5 to 25 weight percent of a pH-dependent binder which is less soluble at lower pH and more soluble at higher pH.

2. A pharmaceutical composition according to claim 1 in which the spherical particles have an area radius to circumference radius ratio of 0.85 to 1.0.

3. A pharmaceutical composition according to claim 1 in which at least 70 weight percent of the spherical particles have diameters which are within upper and lower limits which differ by not more than a factor of the square root of two from each other.

4. A pharmaceutical composition according to claim 1 which provides therapeutic plasma concentrations suitable for twice daily administration of the pharmaceutical composition.

5. A pharmaceutical composition according to claim in which the pH-dependent binder is a single material, or a mixture of materials selected from either of the groups a and b consisting of:

(a) phthalic acid derivatives of vinyl polymers and copolymers, hydroxyalkylcelluloses, alkylcelluloses, cellulose acetates, hydroxylakylcellulose acetates, cellulose ethers, alkylcellulose acetates, and the partial esters thereof; and (b) polymers and copolymers of lower alkyl acrylic acids and lower alkyl acrylates, and the partial esters thereof.

6. A long acting sustained release pharmaceutical dosage form for administration of a therapeutically effective amount of non amorphous Nicardipine hydrochloride, which dosage form consists essentially of an inert pharmaceutical carrier in which is contained:

(a) a long acting pharmaceutical composition according to claim 1 for prolonged administration of non amorphous Nicardipine hydrochloride in combination with (b) a fast release pharmaceutical composition for administration of a loading dose of non amorphous Nicardipine hydrochloride, wherein the relative proportions of long acting pharmaceutical composition and fast release pharmaceutical composition are in the range of 50:50 to 100:0.

7. The pharmaceutical dosage form of claim 6 in which the inert pharmaceutical carrier is a hard gelatin capsule.

8. The pharmaceutical dosage form of claim 6 in which the pH-dependent binder is a copolymer of methacrylic acid and methacrylic or acrylic acid ethyl ester.

9. A method of treating cardiovascular disease in a mammal, which method comprises administering to a mammal in need of such treatment a therapeutically effective amount of a pharmaceutical composition of claim 1.

10. A long acting sustained released pharmaceutical composition suitable for twice daily administration of a therapeutically effective amount of nicardipine hydrochloride, which comprises essentially spherical non-coated, non-rugose particles having an area radius to circumference radius ratio of 0.85 to 1.0 and diameters of about 0.7-1.0 mm and comprising about 10-25 weight percent nicardipine hydrochloride and about 5-25 weight percent of a polymethacrylate which is substantially insoluble below 4.5, wherein at least 70 weight percent of the spherical particles have diameters which are within upper and lower limits differing by not more than the square root of two from each other.

* * * * *

UNITED STATES PATENT AND TRADEMARK OFFICE
CERTIFICATE OF CORRECTION

PATENT NO. : 5,198,226
DATED : March 30, 1993
INVENTOR(S) : MacFarlane, et al.

It is certified that error appears in the above-identified patent and that said Letters Patent is hereby corrected as shown below:

Claim 5, at column 21, lines 43-44: "according to claim in which" should read --according to claim 1 in which--

Claim 5, at column 22, line 1: "hydroxylakylcellulose" should read --hydroxyalkylcellulose--

Claim 6, at column 22, lines 9, 13-14 and 17-18: "non amorphous Nicardipine" should read --non-amorphous nicardipine--

Claim 6, at column 22, line 14: "hydrochloride in combination with" should read --hydrochloride; in combination with--

Claim 10, at column 22, line 35: "released" should read --release--

Claim 10, at column 22, line 37: "amount of nicardipine hydrochloride," should read --amount of non-amorphous nicardipine hydrochloride,--

Signed and Sealed this

Thirty-first Day of May, 1994

Attest:

BRUCE LEHMAN

Attesting Officer

Commissioner of Patents and Trademarks